United States Patent [19]

Meier

[11] Patent Number: 4,789,680
[45] Date of Patent: Dec. 6, 1988

[54] ARALKYLTRIAZOLE COMPOUNDS

[75] Inventor: René Meier, Buus, Switzerland

[73] Assignee: Ciba-Geigy Corporation, Ardsley, N.Y.

[21] Appl. No.: 920,623

[22] Filed: Oct. 20, 1986

Related U.S. Application Data

[63] Continuation-in-part of Ser. No. 733,347, May 13, 1985, abandoned, which is a continuation-in-part of Ser. No. 562,257, Dec. 16, 1983, abandoned.

[30] Foreign Application Priority Data

Dec. 23, 1982 [CH] Switzerland .......................... 7526/82
Oct. 29, 1983 [CH] Switzerland .......................... 5860/83
Apr. 18, 1985 [CH] Switzerland .......................... 1663/85

[51] Int. Cl.$^4$ ................... C07D 249/04; A61K 31/41
[52] U.S. Cl. ..................................... 514/359; 548/255
[58] Field of Search .................. 548/255; 514/359, 340

[56] References Cited

U.S. PATENT DOCUMENTS 4,346,097  8/1982  Schweiss et al ..................... 548/362
4,511,572  4/1985  Kadaba ............................... 514/340

FOREIGN PATENT DOCUMENTS 639376 11/1983 Switzerland.

OTHER PUBLICATIONS

Albert I, C. A. 91:175304h (1979) V-Triazolo[5,4-d] pyrimidines, Part 20, J. Chem. Soc., Perkin Trans. 1, 1978.
Albert II, I95:150600w Part 24, v-Triazolo[4,5-d] pyrimidines J. Chem. Soc., Perkin Trans. 1, 1981(8) pp. 2344–2351.
Lucacchini et al., CA91(25)2042195, J. Ital Biochem., 28(3) pp. 194–206 1979.

*Primary Examiner*—Richard L. Raymond
*Assistant Examiner*—D. L. Dinner
*Attorney, Agent, or Firm*—Irving M. Fishman

[57]  ABSTRACT

1-phenyl-lower alkyl-1H-1,2,3-triazole compounds of the formula

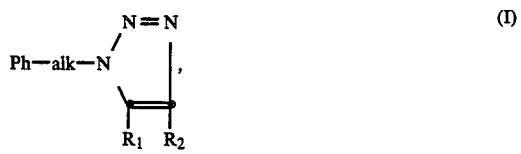

in which
Ph represents phenyl substituted by up to and including 3 substituents selected from lower alkyl, halogen and trifluoromethyl, alk represents lower alkylidene, and wherein either
$R_1$ represents hydrogen, lower alkyl, lower alkoxy, amino, N-lower alkylamino, N,N-di-lower alkylamino, N-lower alkanoylamino, carbamoyl, N-lower alkanoylcarbamoyl, N-lower alkylcarbamoyl or N,N-di-lower alkylcarbamoyl and
$R_2$ represents carbamoyl, N-lower alkanoylcarbamoyl, N-lower alkylcarbamoyl or N,N-di-lower alkylcarbamoyl or
$R_1$ represents carbamoyl, N-lower alkanoylcarbamoyl, N-lower alkylcarbamoyl or N,N-di-lower alkylcarbamoyl and
$R_2$ represents hydrogen or lower alkyl,
have anti-convulsive properties and can be used as medicaments.

21 Claims, No Drawings

ARALKYLTRIAZOLE COMPOUNDS

The invention relates to novel 1-phenyl-lower alkyl-1H-1,2,3-triazole compounds of the formula

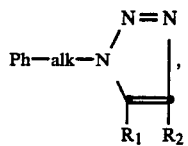

in which

Ph represents phenyl substituted by up to and including 3 substituents selected from lower alkyl, halogen and trifluormethyl, alk represents lower alkylidene, $R_1$ represents hydrogen, lower alkyl, lower alkoxy, amino, N-lower alkylamino, N,N-di-lower alkylamino, N-lower alkanoylamino, carbamoyl, N-lower alkanoylcarbamoyl, N-lower alkylcarbamoyl or N,N-di-lower alkylcarbamoyl and $R_2$ represents carbamoyl, N-lower alkanoylcarbamoyl, N-lower alkylcarbamoyl or N,N-di-lower alkylcarbamoyl or $R_1$ represents carbamoyl, N-lower alkanoylcarbamoyl, N-lower alkylcarbamoyl or N,N-di-lower alkylcarbamoyl and $R_1$ represents hydrogen or lower alkyl,
and to pharmaceutical preparations containing these compounds and to the use thereof.

The phenyl radical Ph contains especially one or two, of the mentioned substituents.

The invention relates, for example, to those compounds of the formula I in which Ph represents phenyl substituted in the 2-position by lower alkyl, halogen or trifluoromethyl and optionally substituted, in addition, by lower alkyl or halogen, which is located, for example, in the 3-, 4- or 6-position, preferably in the 3- or 6-position, alk represents lower alkylidene, $R_1$ represents hydrogen, lower alkyl, lower alkoxy, or an amino group or carbamoyl group that is unsubstituted or substituted by lower alkyl and $R_2$ represents carbamoyl that is unsubstituted or substituted by lower alkyl, to pharmaceutical preparations containing these compounds and to the use thereof.

Amino optionally substituted by lower alkanoyl or lower alkyl is amino, lower alkanoylamino, lower alkylamino or di-lower alkylamino. Likewiese, carbamoyl optionally substituted by lower alkanoyl or lower alkyl is carbamoyl, N-lower alkanoylcarbamoyl, N-lower alkylcarbamoyl or N,N-di-lower alkylcarbamoyl.

By "lower" organic groups and compounds there is to be understood hereinbefore and hereinafter those organic groups and compounds that have up to and including 7, especially up to and including 4, carbon atoms.

Lower alkyl is, for example, methyl, ethyl, propyl, isopropyl, butyl, isobutyl, secondary butyl or tertiary butyl, and also one of the isomeric pentyl, hexyl or heptyl groups.

Halogen is, for example, halogen having an atomic number of up to and including 35, such as fluorine, chlorine or bromine.

Lower alkylidene is, for example, 1,1-lower alkylidene having up to and including 4 carbon atoms, such as methylene, ethylidene, 1,1-propylidene, 1,1-butylidene, but may also be isopropylidene, 1,1-isobutylidene or a 1,1-pentylidene, 1,1-hexylidene or 1,1-heptylidene group.

Lower alkoxy is, for example, methoxy, ethoxy, propoxy, isopropoxy, butoxy, isobutoxy, secondary butoxy or tertiary butoxy, or also one of the isomeric pentyloxy, hexyloxy or heptyloxy groups. N-Lower alkylamino is, for example, straight-chain lower alkylamino having up to and including 4 carbon atoms, such as methyl-, ethyl-, propyl- or butyl-amino, but may be branched lower alkylamino having up to and including 4 carbon atoms, such as isopropyl-, isobutyl- or tertiary butyl-amino, or a pentylamino, hexylamino or heptylamino group. N,N-Di-lower alkylamino is, for example, straight-chain di-lower alkylamino having up to and including 4 carbon atoms in each lower alkyl moiety, such as dimethylamino, diethylamino, methylethylamino, dipropylamino or dibutylamino, but may also be singly branched di-lower alkylamino having up to and including 4 carbon atoms in each lower alkyl moiety, such as methylisopropylamino.

N-lower alkylcarbamoyl is, for example, straight-chain N-lower alkylcarbamoyl having up to an including 4 carbon atoms in the lower alkyl moiety, such as N-methyl-, N-ethyl, N-propyl- or N-butyl-carbamoyl, but may also be branched N-lower alkylcarbamoyl having up to and including 4 lower alkyl carbon atoms, such as N-isopropyl-, N-isobutyl, N-secondary butyl- or N-tertiary butyl-carbamoyl, or a pentylcarbamoyl, hexylcarbamoyl or heptylcarbamoyl group.

N,N-di-lower alkylcarbamoyl is, for example, straight-chain N,N-di-lower alkylcarbamoyl having up to and including 4 carbon atoms in each of the lower alkyl moieties, such as N,N-dimethyl-, N,N-diethyl-, N-ethyl-N-methyl-, N,N-di-propyl- or N,N-dibutyl-carbamoyl, but may also be singly branched N,N-di-lower alkylcarbamoyl having up to an including 4 carbon atoms in each of the lower alkyl moieties, such as N-isopropyl-N-methyl or N-isobutyl-N-methyl-carbamoyl, or an N,N-dipentyl-, N,N-dihexyl- or N,N-diheptyl-carbamoyl group.

The novel compounds have valuable pharmacological properties, especially a marked anti-convulsive activity, which may be demonstrated, for example, in mice in the form of a clear metrazole antagonism in a dosage range of approximately from 30 to 300 mg/kg p.o., and in mice and rats in the form of a marked protective action against convulsions induced by electric shock in a dosage range of approximately from 10–100 mg/kg p.o. (mice) and approximately from 5–50 mg/kg p.o. (rats). The compounds of the formula I are therefore outstandingly suitable for the treatment of convulsions of various origins, for example for the treatment of epilepsy. They can therefore be used as active ingredients in anti-convulsive, for example anti-epileptic, medicaments.

The invention relates especially to, for example, compounds of the formula I in which Ph represents 2-halophenyl, 2-trifluoromethylphenyl, 2-lower alkylphenyl, 2,3- or 2,6-dihalophenyl, 2-halo-3-lower alkylphenyl or 3 halo-2-lower alkylphenyl, 2-halo-6-lower alkylphenyl, 2,3- or 2,6-di-lower alkylphenyl, 3-halo-2-trifluoromethylphenyl or 2-halo-3-trifluoro-methylphenyl or 2-halo-6-trifluoromethylphenyl, alk represents 1,1-lower alkylidene, $R_1$ represents either amino or hydrogen, lower alkyl, lower alkoxy, carbamoyl, N-lower alkylcarbamoyl or N,N-di-lower alkylcarbamoyl, and $R_2$ represents carbamoyl, N-lower alkylcarbamoyl or N,N-di-lower alkylcarbamoyl, lower alkyl and lower alkyl in N-lower alkyl-amino or -carbamoyl and N,N-di-lower alkyl-amino or -carbamoyl, lower alkyl, lower alkoxy and lower alkylidene having, for example, up to and including 7 carbon atoms.

The invention relates especially also to compounds of the formula I in which Ph represents phenyl substituted by up to and including 3 substituents selected from lower alkyl groups, halogen atoms and trifluoromethyl, lower alkyl having up to and including 4 carbon atoms and, for example, being methyl, and halogen having an atomic number of up to and including 35, that is to say fluorine, chlorine or bromine, for example: 2-lower alkylphenyl, 2- or 3-halophenyl, 2-trifluoromethylphenyl, 2,3- or 2,6-di-lower alkylphenyl or 2,3-, 2,4- or 2,6-dihalophenyl, alk represents 1,1-lower alkylidene having up to an including 4 carbon atoms, for example methylene, ethylidene or 1,1-propylidene, $R_1$ represents amino or lower alkanoylamino of up to and including 7 carbon atoms, for example acetylamino, and $R_2$ represents carbamoyl, N-lower alkanoylcarbamoyl of up to and including 7 carbon atoms, N-lower alkyl- or N,N-di-lower alkylcarbamoyl having up to and including 4 carbon atoms in each lower alkyl moiety, such as carbamoly, N-acetylcarbamoyl, N-methylcarbamoyl or N,N-dimethylcarbamoyl.

The invention relates more especially to compounds of the formula I in which a lower alkyl substituent in Ph is lower alkyl having up to and including 4 carbon atoms, for example methyl or ethyl, and a halogen substituent in Ph is halogen having an atomic number of up to and including 35, for example chlorine, and Ph represents 2-halophenyl, such as 2-fluoro-, 2-chloro- or 2-bromo-phenyl, 2-trifluoromethylphenyl, 2-lower alkylphenyl, such as 2-methyl- or 2-ethylphenyl, 2,3- or 2,6-dihalophenyl, for example 2,6-dichlorophenyl, or 2,3- or 2,6-di-lower alkylphenyl, such as 2,3-dimethylphenyl, alk represents 1,1-lower alkylidene having up to and including 4 carbon atoms, for example methylene, ethylidene or 1,1-propylidene, $R_1$ represents amino and $R_2$ represents carbamoyl.

The invention relates even more especially to compounds of the formula I, wherein Ph denotes o-halophenyl, such as o-fluoro- or o-chlorophenyl, m-halophenyl, such as m-chlorophenyl, 2,6-dihalophenyl, such as 2,6-difluoro- or 2,6-dichlorophenyl, o-lower alkylphenyl of from 7 up to and including 10 carbon atoms, such as o-methylphenyl, or m-trifluormethylphenyl, alk denotes 1,1-alkylidene of up to and including 4 carbon atoms, such as methylene or 1,1-propylene, $R_1$ denotes either amino or carbamoyl and $R_2$ represents carbamoyl or in which Ph represents o-halophenyl or 2,6-dihalophenyl, alk denotes 1,1-alkylidene of up to and including 4 carbon atoms, such as methylene or 1,1-propylene, $R_1$ represents hydrogen or lower alkyl of up to and including 4 carbon atoms, such as methyl, and $R_2$ represents carbamoyl.

The invention relates most especially to the compounds of the formula I described in the Examples.

The compounds of the formula I can be manufactured by methods known per se, for example as follows: an azide of the formula

Ph—alk—N$_3$  (II)

is reacted with a compound of the formula

in which $R_2'$ represents a carbamoyl group that is unsubstituted or substituted by acyl or lower alkyl, $Y_1$ represents an amino group disubstituted as indicated hydrogen, lower alkyl, lower alkocy or carbamoyl that is unsubstituted or substituted as indicated, and $Y_2$ and $Y_3$ together represent an additional bond, or in which $R_2'$ represents a carbamoyl group that is unsubstituted or substituted by acyl or lower alkyl, $Y_1$ and $Y_2$ together represent imino and $Y_3$ is hydrogen, or with a tautomer and/or salt thereof, if necessary a resulting isomeric mixture is separated into its components and the isomer of the formula I is isolated and, if desired, the compound obtainable according to the process is converted into a different compound of the formula formula I.

Tautomers of compounds of the formula III are, for example, cyanoacetyl tautomers of the formula N≡C—CH$_2$—R$_2'$ (IIIa) of ketimine compounds of the formula III in which $Y_1$ and $Y_2$ represent imino and $Y_3$ represents hydrogen.

Salts of compounds of the formula III are, for example, metal salts, such as alkali metal salts, of compounds of the formula III in which $Y_1$ and $Y_2$ together represent imino and $Y_3$ represents hydrogen, or the tautomers thereof of the formula IIIa.

The reaction is carried out in customary manner, advantageously in an inert solvent, if necessary in the presence of a condensation agent and/or at elevated temperature. Inert solvents are, for example, aromatic or araliphatic hydrocarbons, such as benzene or toluene, or ethers, such as tertiary butoxymethane, tetrahydrofuran or dioxane, and, for the reaction with compounds of the formula IIIa, also alcohols, such as lower alkanols, for example methanol, ethanol or butanol. Condensation agents are, for example for the reaction with compounds of the formula III in which $Y_1$ and $Y_2$ together represent imino and $Y_3$ represents hydrogen, or the tautomers thereof of the formula IIIa, salt-forming condensation agents, such as metal alcoholates, for example sodium methoxide, sodium ethoxide, or other alkali metal lower alkoxides, metal amides, such as sodium amide, lithium diisopropyl amide and the like, or organometal compounds, such as lower alkylmagnesium halides or lower alkyllithium compounds, for example methyl- or butyl-magnesium bromide or butyllithium. Instead of carrying out the process in the presence of one of the mentioned condensation agents, the component of the formula III or IIIa may alternatively be used in the form of a salt.

Preferred embodiments of this process are, for example, the reaction of an azide of the formula II with a compound of the formula III in which $Y_1$ represents hydrogen or lower alkyl, and $Y_2$ and $Y_3$ represent an additional bond, in benzene or dioxan at approximately from 60°–120° C., preferably at boiling temperature, and the reaction with compounds of the formula IIIa in the presence of sodium methoxide or sodium ethoxide and methanol or ethanol, respectively, as the solvent, at approximately from 40° to 100° C., preferably at the boiling temperature.

The starting materials of the formula III and some of those of the formula II are known. Novel starting materials of the formula II can be obtained analogously to the method of formation of the known starting materials, for example by reacting a compound of the formula Ph—alk—X (IV), in which X represents reactive esterified hydroxy, such as halogen, for example chlorine, bromine or iodine, or sulphonyloxy, such as lower alkanesulphonyloxy, optionally substituted benzenesulphonyloxy, such as methane-, ethane-, benzene-, p-toluene- or p-bromobenzene-sulphonyloxy, or fluorosulphonyloxy, with an alkali metal azide, for example with sodium azide, for example in dimethylsulphoxide or dimethylformamide, or by reacting an alcohol of the formula IV (X =hydroxy), in the presence of triphenylphosphine and an azodicarboxylic acid ester, for example azodicarboxylic acid diethyl ester, with hydrazoic acid, for example in toluene.

The novel compounds may also be manufactured as follows: a compound of the formula Ph—alk—Z 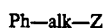 (IV)

in which Z represents reactive esterified hydroxy is reacted with a 1H-1,2,3-triazole derivative of the formula

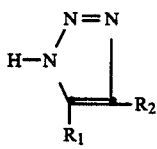 (V)

or a salt thereof, if necessary a resulting isomeric mixture is separated into its components and the isomer of the formula I is isolated and, if desired, the compound obtainable according to the process is converted into a different compound of the formula I.

Reactive esterified hydroxy Z is, for example, halogen, for example chlorine, bromine or iodine, or sulphonyloxy, such as lower alkanesulphonyloxy, optionally substituted benzenesulphonyloxy, such as methane-, ethane-, benzene-, p-toluene- or p-bromobenzene-sulphonyloxy, or fluorosulphonyloxy.

Salts of compounds of the formula V are, for example, alkali metal or alkaline earth metal salts, such as sodium, potassium or calcium salts.

The reaction is carried out in customary manner, for example in the presence of a basic condensation agent or, advantageously, using the component of the formula V in the form of a salt, if necessary while heating, preferably in a solvent or diluent. Basic condensation agents are, for example, basic condensation agents that form salts with the component of the formula V, such as alkali metal alcoholates, for example sodium methoxide or sodium ethoxide, alkali metal or alkaline earth metal amides, for example sodium amide or lithium diisopropyl amide. As mentioned, the conversion of the component of the formula V into one of its salts is preferably carried out in advance, for example by reaction with one of the above-mentioned bases. Solvents for carrying out the reaction in the presence of an alcoholate are preferably the corresponding alcohols and, for carrying out the reaction in the presence of amides, are, for example, aprotic organic solvents, such as phosphoric acid lower alkylamides or di-lower alkylsulphoxides, for example hexamethylphosphoric acid triamide or dimethylsulphoxide respectively.

The process is suitable especially for the manufacture of compounds in which an amino group $R_1$ or the amino group as a constituent of a carbamoyl group $R_2$ is at least N-mono-substituted, and preferably N,N-di-substituted, that is to say represents acylamino, lower alkylamino or preferably di-lower alkylamino, lower alkyleneamino or (N'-lower alkyl) aza-, oxa- or thia-lower alkyleneamino.

The starting materials of the formulae IV and V that are not already known can be manufactured in customary manner. Thus, compounds of the formula IV are obtained, for example, by reactively esterifying a corresponding alcohol of the formula IV (Z =hydroxy), for example by means of thionyl chloride, phosphorus tribromide or a sulphonyl chloride. Compounds of the formula V can be manufactured as follows: hydrazoic acid or trimethylsilylazide is reacted with a compound of the formula

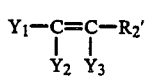 (III)

in which $R_2'$ represents a carbamoyl group that is unsubstituted or substituted by acyl or lower alkyl, $Y_1$ represents an amino group disubstituted as indicated, hydrogen, lower alkyl, lower alkoxy or carbamoyl that is unsubstituted or substituted as indicated, and $Y_2$ and $Y_3$ together represent an additional bond, or in which $R_2'$ represents a carbamoyl group that is unsubstituted or substituted by acyl or lower alkyl, $Y_1$ an $Y_2$ together represent imino and $Y_3$ represents hydrogen, or with a tautomer and/or salt thereof and, if desired, an amino group, $R_1$ and/or a carbamoyl group, $R_2$ is acylated or lower-alkylated and in a 1-trimethylsilyl triazole derivative so obtained, the trimethylsilyl group is subsequently removed by mild hydrolysis.

The novel compounds can also be manufactured as follows: in a compound of the formula

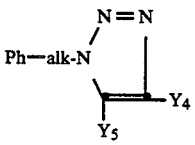 (VI)

in which $Y_4$ represents a radical $Y_A$ and $Y_5$ represents an $R_1$ group or a radical $Y_B$, or $Y_4$ represents an $R_2$ group and $Y_5$ represents a radical $Y_B$, $Y_A$ representing a radical that can be converted into carbamoyl that is unsubstituted or substituted as indicated, and $Y_B$ representing a radical that can be converted into carbamoyl optionally substituted as indicated, or in a salt thereof, $Y_A$ is converted into carbamoyl optionally substituted as indicated, and/or $Y_B$ is converted into carbamoyl optionally substituted as indicated, and $Y_B$ representing a radical that can be converted into carbamoyl optionally substituted as indicated, or in a salt thereof, $Y_A$ is converted into carbamoyl optionally substituted as indicated, and/or $Y_B$ is converted into carbamoyl optionally substituted as indicated, if necessary a resulting isomeric mixture is separated into its components and the isomer of the formula I is isolated and, if desired, the compound obtainable according to the process is converted into a different compound of the formula I.

Radicals $Y_A$ and $Y_B$ according to the above definition are, for example, free carboxy groups or carboxy groups present in salt or anhydride form, amidino groups that are optionally N-lower alkylated or N,N- disubstituted by lower alkylene or by aza-, oxa- or thia-lower alkylene, or esterified carboxy groups also cyano groups.

Esterified carboxy groups are, for example, carboxy groups esterified by a lower alkanol or a lower alkyl-mercaptan, that is to say, lower alkoxy- or lower alkylthio-carbonyl groups, but may also be esterified by any other alcohol or mercaptan, for example by an optionally substituted phenol or thiophenol.

Carboxy groups present in salt form are, for example, carboxy groups present in an ammonium salt form derived from ammonia or a mono- or di-lower alkylamine, or also carboxy groups present in metal salt form, for example in alkali metal or alkaline earth metal salt form.

Carboxy groups present in anhydride form are, for example, carboxy groups present in the form of a halide, such as chlorocarbonyl, but may also be anhydridised by a reactive carboxylic acid, and represent for example, alkoxycarbonyloxycarbonyl or trifluoroacetoxycarbonyl.

Amidino groups optionally lower alkylated or N,N-di-substituted by lower alkylene or by aza-, oxa- or thia-lower alkylene are, for example, amidino groups that are unsubstituted or N-mono-, N,N-di- or N,N'-di-lower alkylated.

The conversion of the above-mentioned groups $Y_4$ or $Y_5$ into carbamoyl optionally substituted as indicated, is carried out in customary manner, using as the starting materials carboxy groups that are free, esterified or in anhydride form and amidino groups that are optionally N-lower alkylated by means of solvolysis, that is to say hydrolysis, or ammonolysis or aminolysis (reaction with ammonia or with a mono- or di-lower alkylamine.

By means of hydrolysis, for example amidino groups $Y_4$ and/or $Y_5$ that are optionally lower alkylated, can be converted into optionally correspondingly substituted carbamoyl, and cyano $Y_4$ and/or $Y_5$ can be converted into carbamoyl. The hydrolysis is carried out, for example, in the presence of an acidic hydrolysing agent, such as a mineral, sulphonic or carboxylic acid, for example sulphuric acid, phosphoric acid, hydrochloric acid or a different hydrohalic acid, p-toluenesulphonic acid or a different organic sulphonic acid, or a lower alkanoic acid, such as acetic acid, preferably in catalytic amounts. Cyano $Y_4$ and/or $Y_5$ can also be hydrolysed to form carbamoyl, for example under basic conditions, such as in the presence of an alkali metal hydroxide, but cyano can also be converted into N-lower alkyl- or N,N-di-lower alkyl-carbamoyl, for example by first converting the nitrile of the formula I, for example by treatment with a lower alkanol, phenol or any other alcohol, into an imino ether, reacting the latter with a mono- or di-lower alkylamine, and hydrolysing the amidine formed, preferably under mildly acidic conditions.

By means of ammonolysis or aminolysis, for example carboxy groups that are free, present in salt form or esterified can be converted into carbamoyl that is unsubstituted or substituted as indicated. The operation is carried out, if necessary, in the presence of a condensation agent, advantageously in an inert solvent. Using carboxy in anhydride form as the starting material, condensation agents are, for example, basic condensation agents, such as alkali metal hydroxides or carbonates, or organic nitrogen bases, such as amines, in excess, corresponding to the amino group to be introduced, or tertiary organic nitrogen bases, such as tri-lower alkylamines or tertiary heteroaromatic nitrogen bases, such as triethylamine or pyridine, and, using esterified carboxy as the starting material, acidic condensation agents, such as mineral acids, such as hydrohalic acids and the like. Free carboxy groups can be converted into optionally lower alkylated carbamoyl by dehydrating the ammonium salts formed as intermediates, for example by heating or by the action of dehydrating agents, such as acid anhydrides, for example phosphorus pentoxide, acetyl chloride and the like, or carbodiimides, for example N,N'-dicyclohexyl carbodiimide.

The starting materials of the formula VI that are not already known can be manufactured in customary manner, for example as follows: an azide of the formula

$$Ph—alk—N_3 \qquad (II)$$

is reacted with a compound of the formula

in which $Y_1$ represents a group $Y_5$ and $Y_2$ and $Y_3$ represent an additional bond, or $Y_1$ represents hydrogen or lower alkyl, $Y_2$ represents hydroxy and $Y_3$ represents hydrogen, or $Y_1$ and $Y_2$ together represent imino and $Y_3$ represents hydrogen, or with a tautomer and/or salt thereof, for example as described for the reaction with the corresponding compounds of the formula III.

Starting materials of the formula VI in which $Y_5$ represents lower alkoxy and $Y_4$ represents a $Y_A$ group may also be manufactured as follows: an azide of the formula II is reacted with an acid of the formula HOO-C—$CH_2$—$Y_A$ (XI), or an ester, such as a lower alkyl ester, thereof, for example a malonic acid di-lower alkyl ester, and/or a salt thereof, preferably in the presence of an alkali metal alkoxide and, in the 5-hydroxy—1—Ph—alk—4—$Y_A$—1H—1,2,3-triazole formed, the hydroxy group is lower alkylated, preferably by reaction with a reactive lower alkyl ester, such as dimethyl sulphate, in the presence of sodium hydroxide.

The novel compounds may also be manufactured by removing H—$Y_6$ from a compound of the formula

in which $Y_6$ represents a removable radical, and, if necessary, separating a resulting isomeric mixture into its components and isolating the isomer of the formula I and, if desired, converting the compound obtainable according to the process into a different compound of the formula I.

Removable radicals $Y_6$ are, for example, hydroxy, lower alkoxy or optionally substituted amino groups, lower alkoxy preferably being identical to lower alkoxy $R_1$ and optionally substituted amino preferably being identical to free or substituted amino $R_1$.

The removal of H—$Y_6$ generally takes place spontaneously; in individual cases the supply of thermal energy or the presence of an acidic or basic agent, such as a mineral acid, for example sulphuric or hydrochloric acid, or a carboxylic or sulphonic acid, for example acetic or p-toluenesulphonic acid, or an alkali metal hydroxide or alcoholate, for example sodium methoxide, can be advantageous.

The starting materials of the formula IX are preferably manufactured in situ and reacted further without being isolated, for example by reacting a compound of the formula $$Ph\text{—}alk\text{—}N_3 \qquad (II)$$

with a compound of the formula

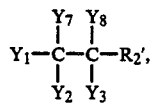

(X)

in which $R_2'$ represents a carbamoyl group that is unsubstituted or substituted by lower alkyl $Y_1$ and $Y_2$ represent lower alkoxy or optionally substituted amino $R_1$, $Y_3$ represents hydrogen and $Y_7$ and $Y_8$ represent an additional bond, or $Y_1$, $Y_2$ and $Y_7$ represent lower alkoxy and $Y_3$ and $Y_8$ represent hydrogen, or $Y_1$ and $Y_2$ together represent oxo, $Y_7$ represents hydrogen or lower alkyl and $Y_3$ and $Y_8$ represent hydrogen, or with a tautomer and/or salt thereof, for example with a compound of the formula $Y_1'\text{-}C(=O)\text{-}CH_2\text{-}R_2'$ (Xa; $Y_1'$ =hydrogen or lower alkyl), $Y_1\text{-}C(Y_2)=CH\text{-}R_2'$(Xb; $Y_1$ and $Y_2$ =lower alkoxy or, independently of one another, amino that is unsubstituted or substituted as indicated for $R_1$), or $Y_1\text{-}C(Y_2)(Y_7)\text{-}CH_2\text{-}R_2'$ (Xc; $Y_1$, $Y_2$ and $Y_7$=lower alkoxy).

Compounds of the formula I in which $R_1$ represents lower alkoxy may also be manufactured as follows: in a compound of the formula

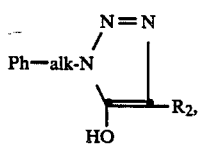

(XII)

the hydroxy group is converted into lower alkoxy and, if necessary, a resulting isomeric mixture is separated into its components and the isomer of the formula I is isolated and, if desired, the compound obtainable according to the process is converted into a different compound of the formula I.

The conversion of hydroxy into lower alkoxy is effected, for example, by reaction with a reactive lower alkyl ester, such as a hydrohalic, such as hydrochloric, hydrobromic or hydriodic, acid ester, a sulphuric acid ester, that is to say a di-lower alkyl sulphate, or a sulphonic acid ester, such as a lower alkane- or optionally substituted benzene-sulphonic acid ester, for example methane-, benzene-, p-toluene-or p-bromobenzene-sulphonic acid ester of a lower alkanol, advantageously in the presence of a basic agent, such as an alkali metal hydroxide, carbonate or alcoholate, for example sodium or potassium hydroxide, potassium carbonate or sodium methoxide, or a tertiary organic nitrogen base, such as a tri-lower alkylamine, for example triethylamine, or pyridine.

The starting materials of the formula XII can be obtained, for example, by reacting an azide of the formula $$Ph\text{—}alk\text{—}N_3 \qquad (II)$$

with an acid of the formula $HOOC\text{-}CH_2\text{-}R_2$ (XI) or an ester, for example a lower alkyl ester, thereof, for example as indicated for the reaction with compounds of the formula IIIa.

Compounds obtainable according to the process can be converted into different compounds of the formula I by converting one or more variables of the general formula I into different variables. Thus, a primary amino $R_1$ can be converted into acylamino or into mono- or di-lower alkylamino. Also mono-lower alkylamino $R_1$ can be converted into di-lower alkylamino. The acylation is effected, for example, by means of a corresponding acid anhydride or chloride, such as acetanhydride, the mixed anhydride of formic and acetic acid, a chloro- or bromoformic acid lower alkylester, methanesulphonylchloride or dimethylcarbamoylchloride, if necessary, in the presence of a base, such as triethylamine or pyridine, or with an inorganic acid, e.g. sulphuric acid. Alkylating agents are, for example, reactive esters of a lower alkanol, such as a lower alkylhalide, for example, a lower alkyl bromide or iodide, lower alkylsulphonate, for example a lower alkylmethanesulphonate or p-toluenesulphonate, or a di-lower alkyl sulphate, for example dimethyl sulphate, preferably under basic conditions, such as in the presence of sodium hydroxide solution or potassium hydroxide solution and advantageously a phase transfer catalyst, such as tetrabutylammonium bromide or benzyltrimethylammonium chloride. In an entirely analogous manner, also carbamoyl $R_2$ and/or $R_1$ can be converted into N-acylcarbamoyl, N-mono- or N,N-di-lower alkylcarbamoyl and N-mono-lower alkylcarbamoyl can be converted into N,N-di-mono-lower alkylcarbamoyl can be converted into N,N-di-lower alkylcarbamoyl, but stronger basic condensation agents, such as alkali metal amides or alcoholates, for example sodium amide or sodium methoxide, may be necessary.

Depending on the choice of starting materials and procedures, the novel compound can be in the form of one of the possible isomers, for example with respect to the position of $R_1$ and $R_2$, or in the form of mixtures thereof, and, depending on the number of asymmetrical carbon atoms, also in the form of optical isomers, such as antipodes, or mixtures thereof, such as racemates, diastereoisomeric mixtures or racemic mixtures.

Resulting mixtures of position isomers as well as diastereoisomeric mixtures and racemic mixtures can be separated on the basis of the physical and chemical differences between their constituents in known manner into the pure position isomers, diastereoisomers and racemates, respectively, for example by chromatography and/or fractional crystallisation. Resulting racemates can also be separated by known methods into the optical antipodes, for example by recrystallisation from an optically active solvent, with the aid of microorganisms or by reaction of an acidic precursor, for example of the formula VI ($Y_4$ and/or $Y_5$=carboxy), with an optically active alcohol that forms esters with the racemic acid and separation of the esters obtained in this manner, for example on the basis of their different solubilities, into the diastereoisomers from which the antipodes can be freed by the action of suitable agents. Advantageously, the more active of the two antipodes is isolated.

Racemates of salt-forming compounds of the formula I can also be split by reaction with an optically active auxiliary compound into diastereoisomeric mixtures, for example with an optically active acid into mixtures of diastereoisomeric acid addition salts, and separation of the latter into the diastereoisomers from which the enantiomers can be freed in the customary manner in each case. Optically active acids customary for this purpose are, for example D- or L-tartaric acid, di-o-toluyltartaric acid, malic acid, mandelic acid, camphorsulphonic acids or quinic acid.

In addition, resulting free salt-forming compounds can be converted in a manner known per se into acid addition salts, for example by reacting a solution of the free compound in a suitable solvent or solvent mixture with one of the above-mentioned acids or with a solution thereof, or with a suitable anion exchanger.

Resulting acid addition salts can be converted in a manner known per se into the free compounds, for example by treatment with a base, such as an alkali metal hydroxide, a metal carbonate or bicarbonate, or ammonia, or with a suitable anion exchanger.

Resulting acid addition salts can be converted in a manner known per se into different acid addition salts, for example by treating a salt of an organic acid with a suitable metal salt, such as a sodium, barium or silver salt, of an acid in a suitable solvent in which the resulting organic salt is insoluble and thus separates out from the reaction mixture.

The compounds, including their salts, can also be obtained in the form of the hydrates or include the solvent used for crystallisation.

As a result of the close relationship between the novel compounds in the free form and in the form of their salts, hereinbefore and hereinafter the free compounds or their salts are to be understood, where appropriate and expedient, to include optionally also the corresponding salts or free compounds.

The invention also relates to those embodiments of the process according to which a compound obtainable as an intermediate at any stage of the process is used as the starting material and the remaining steps are carried out, or a starting material is used in the form of a salt or, especially, is formed under the reaction conditions.

Thus all intermediates of the formula IX can be formed in situ in accordance with the process variant of the reaction of compounds of the formulae II and X, and reacted further without being isolated.

The invention also relates to novel starting materials of the formulae II, V, VI, IX and XII which have been developed especially for the manufacture of the compounds according to the invention, especially the range of starting materials leading to the compounds of the formula I that are characterised as being preferred at the beginning, to the processes for their manufacture and to their use as intermediates.

The novel compounds of the formula I can be used, for example, in the form of pharmaceutical preparations that contain a therapeutically effective amount of the active ingredient, optionally together with inorganic or organic, solid or liquid, pharmaceutically acceptable carriers, and are suitable for enteral, for example oral, or parenteral administration. Thus tablets or gelatine capsules are used which contain the active ingredient together with diluents, for example lactose, dextrose, saccharose, mannitol, sorbitol, cellulose and/or glycine, and/or glidants, for example silica, talc, stearic acid or salts thereof, such as magnesium stearate or calcium stearate, and/or polyethylene glycol. Tablets may also contain binders, for example magnesium aluminium silicate, starches such as corn, wheat, rice or arrowroot starch, gelatine, tragacanth, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorption agents, dyes, flavourings and sweeteners. In addition, the novel compounds of the formula I can be used in the form of preparations that can be administered parenterally, or in the form of infusion solutions. Such solutions are preferably isotonic aqueous solutions or suspensions, it being possible for these to be manufactured before use, for example in the case of lyophilised preparations which contain the active ingredient alone or together with a carrier, for example mannitol. The pharmaceutical preparations may be sterilised and/or contain adjuncts, for example preservatives, stabilisers, wetting agents and/or emulsifiers, solubilisers, salts for regulating the osmotic pressure and/or buffers. The present pharmaceutical preparations, which, if desired, may contain further pharmacologically active substances, are manufactured in a manner known per se, for example by means of conventional mixing, granulating, confectioning, dissolving or lyophilising processes, and contain, from approximately 0.1% to 100%, especially from approximately 1% to approximately 50%, and in the case of lyophilisates up to 100%, of the active ingredient.

The invention also relates to the use of the compounds of the formula I, preferably in the form of pharmaceutical preparations. The dosage can depend on various factors, such as the method of administration, and the species, age and/or condition of the individual. The doses to be administered daily in the case of oral administration are between approximately 5 and approximately 50 mg/kg and for warm blooded animals weighing approximately 70 kg preferably between approximately 0.5 g and approximately 5.0 g.

The following Examples serve to illustrate the invention; temperatures are given in degrees Centigrade.

EXAMPLE 1

23 g (1 mol) of sodium are dissolved in 1 litre of ethyl alcohol and 101 g (1.2 mol) of cyanoacetamide are added thereto. 167.5 g (1 mol) of o-chlorobenzyl azide are added to this suspension at 40°–45° and the whole is heated for 2 hours under reflux. After cooling to 30°, 1000 ml of water are added, the precipitated product is filtered off with suction and then washed several times with warm water. After recrystallisation from dioxan and toluene, 5-amino-1-(o-chlorobenzyl)-1H-1,2,3-triazole-4-carboxamide is obtained in the form of colourless crystals having a melting point of 206°–207°.

EXAMPLE 2

In analogous manner, starting from 2,6-dichlorobenzyl azide, there is obtained 5-amino-1-(2,6-dichlorobenzyl)-1H-1,2,3-triazole-4-carboxamide having a melting point of 243°–245° (after crystallisation from methanol).

The starting material can be prepared, for example, as follows:

24 g (0.1 mol) of 2,6-dichlorobenzyl bromide in 50 ml of dimethyl sulphoxide are added at room temperature to a suspension of 7.2 g (0.11 mol) of sodium azide in 50 ml of dimethyl sulphoxide and the whole is stirred for 2 hours at room temperature. The mixture is then diluted with 250 ml of water and extracted with cyclohexane and the organic phase is washed several times with water. After drying over sodium sulphate, the cyclohexane is distilled off in vacuo at 50°. 2,6-dichlorobenzyl azide is obtained in the form of a colourless liquid. It is used without further purifification.

EXAMPLE 3

In a manner analogous to that described in Example 2, starting from o-methylbenzyl chloride, there is obtained via α-azido-o-xylene, 5-amino-1-(o-methylbenzyl)-1H-1,2,3-triazole-4-carboxamide having a melting point of 227°–228° (after crystallisation from dioxan/ethanol).

EXAMPLE 4

In a manner analogous to that described in Example 1, starting from o-fluorobenzyl azide, there is obtained 5-amino-1-(o-fluorobenzyl)-1H-1,2,3-triazole-4-carboxamide having a melting point of 189°–190° (from methanol).

EXAMPLE 5

In a manner analogous to that described in Example 1, starting from o-bromobenzyl azide, there is obtained 5-amino-1-(o-bromobenzyl)-1H-1,2,3-triazole-4-carboxamide having a melting point of 211°–213° (from ethanol).

EXAMPLE 6

In a manner analogous to that described in Example 1, starting from o-trifluoromethylbenzyl azide, there is obtained 5-amino-1-(o-trifluoromethylbenzyl)-1H-1,2,3-triazole-4-carboxamide having a melting point of 197°–198° (from methanol).

The starting material can be prepared, for example, as follows:

First a solution of 17.4 g (0.1 mol) of azodicarboxylic acid diethyl ester in 50 ml of toluene is added dropwise at 10°–20° to a solution of 26.2 g (0.1 mol) of triphenylphosphine in 260 ml of toluene and then, at 5°–10°, a solution of 17.6 g (0.1 mol) of o-trifluoromethylbenzyl alcohol in 120 ml of a 1N solution of hydrazoic acid in toluene is added dropwise thereto and the whole is stirred at room temperature for 2 hours. The precipitated hydrazinodicarboxylic acid ester is filtered off with suction, the toluene solution is concentrated by evaporation and the residue is treated with cyclohexane. The cyclohexane solution is decanted off from the insoluble portions, filtered through a small amount of silica gel and concentrated by evaporation at 50° in vacuo. In this manner o-trifluoromethylbenzyl azide is obtained in the form of a colourless liquid.

EXAMPLE 7

In a manner analogous to that described in Example 6, starting from 2,3-dimethylbenzyl alcohol, there is obtained via 2,3-dimethylbenzyl azide 5-amino-1-(2,3-dimethylbenzyl)-1H-1,2,3-triazole-4-carboxamide having a melting point of 217°–219° (from ethyl acetate).

EXAMPLE 8

In a manner analogous to that described in Example 2, starting from 1-(o-chlorophenyl)-phenethyl chloride, there is obtained via 1-(o-chlorophenyl)-ethyl azide 5-amino-1-[1-(o-chlorophenyl)-ethyl]-1H-1,2,3-triazole-4-carboxamide having a melting point of 202°–204° (from ethanol).

EXAMPLE 9

In a manner analogous to that described in Example 2, starting from 1-(o-chlorophenyl)-propyl chloride, there is obtained via 1-(o-chlorophenyl)-propyl azide 5-amino-1-[1-(o-chlorophenyl)-propyl]-1H-1,2,3-triazole-4-carboxamide having a melting point of 152°–153° (from ethanol).

EXAMPLE 10

In a manner analogous to that described in Example 6, starting from 1-(o-chlorophenyl)-butanol, there is obtained via 1-(o-chlorophenyl)-butyl azide 5-amino-1-[1-(o-chlorophenyl)-butyl]-1H-1,2,3-triazole-4-carboxamide having a melting point of 150°–152° (from methanol).

EXAMPLE 11

25.2 g (0.1 mol) of 5-amino-1-(o-chlorobenzyl)-1H-1,2,3-triazole-4-carboxamide are dissolved in 100 ml of dimethylformamide and, while stirring at 0°, 30.6 g (0.2 mol) of phosphorus oxychloride are added dropwise. The whole is then heated rapidly until the reaction mixture has reached 80° and then cooled again immediately to 20°. At this temperature, 100 ml of 1N hydrochloric acid are added dropwise and then the whole is heated rapidly and maintained for 5 minutes under reflux. The hot reaction solution is diluted with 400 ml of water and the precipitated product is filtered off with suction. After washing several times with water and subsequent crystallisation from ethyl alcohol, there is obtained 5-amino-1-(o-chlorobenzyl)-1H-1,2,3-triazole-4-carboxylic acid nitrile having a melting point of 174°–176°. This compound can also be obtained in the following, different manner: 1.15 g of sodium are dissolved in 50 ml of ethanol. A mixture of 8.4 g of o-chlorobenzyl azide, 3.3 g of malodinitrile and 50 ml of ethanol are then added, the whole is left to stand for 24 hours at room temperature and the solvent is distilled off under reduced pressure. The residue is shaken with 50 ml of 2N hydrochloric acid and 100 ml of ethyl acetate, the organic phase is separated off and concentrated by evaporation, and the residue is recrystallised twice from ethanol. Likewise obtained in this manner is 5-amino-1-(o-chlorobenzyl)-1H-1,2,3-triazole-4-carboxylic acid nitrile, having a melting point of 174°–176°.

10 ml of a 30% strenth hydrogen peroxide solution are added at 40°–50° to a solution of 11,7 g (0.05 mol) of 5-amino-1-(o-chlorobenzyl)-1H-1,2,3-triazole-4-carboxylic acid nitrile in 150 ml of ethanol and 25 ml of 2N sodium hydroxide solution. The reaction mixture is stirred for 2,5 hours at 40°–50° and then diluted with 250 ml of water and the precipitate is filtered off. The crude product is re-crystallised from dioxan and voluene yielding 5-amino-1-(o-chlorobenzyl)-1H-1,2,3-triazole-4-carboxamide of melting point 206°–208°, A solution of 11.7 g (0.05 mol) of 5-amino-1-(o-chlorobenzyl)-1H-1,2,3-triazole-4-carboxylic acid nitrile and 21.3 g (0.15 mol) of methyl iodide in 250 ml of acetonitrile is added dropwise at 20°–25° to a stirred suspension of 11.2 g of pulverised potassium hydroxide and 1.6 g (0.005 mol) of tetrabutylammonium bromide in 100 ml of acetonitrile. After 1 hour, the inorganic material is decanted off and the acetonitrile is evaporated off in vacuo. The residue is dissolved in diethyl ether, undissolved material is filtered off and the ether solution is filtered through silica gel. After evaporation of the ether, there is obtained 1-(o-chlorobenzyl)-5- dimethylamino-1H-1,2,3-triazole-4-carboxylic acid nitrile having a melting point of 64°–67°.

25 ml of a 30% strength hydrogen peroxide solution are added dropwise at 40°–50° to a solution of 13.1 g (0.05 mol) of 1-(o-chlorobenzyl)-5-dimethyl-amino -1H-1,2,3-triazole-4-carboxylic acid nitrile in 300 ml of ethanol and 25 ml of 5N sodium hydroxide solution. When the dropwise addition is complete, the whole is stirred for 2 hours at 40°–50° and then diluted with 600 ml of water and the precipitated product is filtered off with suction. After washing with water and crystallisation from 70% strength ethanol, there is obtained 1-(o-chlorobenzyl)-5-dimethylamino-1H-1,2,3-triazole-4-carboxamide having a melting point of 164°–166°.

EXAMPLE 12

93 g (0.03 mol) of 1-(o-chlorobenzyl)-1H-1,2,3-triazole-4,5-dicarboxylic acid dimethyl ester are dissolved in 250 ml of methanol and saturated with ammonia at 50°. After being left to stand for 3 days at 60°, the reaction solution is cooled and the product that has crystallised out is filtered off with suction and washed with methanol. In this manner there is obtained 1-(o-chlorobenzyl)-1H-1,2,3-triazole-4,5-dicarboxamide having a melting point of 222°–224°.

The starting material can be prepared, for example, as follows:

A solution of 8 g (0.054 mol) of acetylene-dicarboxylic acid dimethyl ester in 25 ml of benzene is added dropwise to a solution of 8.4 g (0.05 mol) of o-chlorobenzyl azide in 50 ml of benzene that is boiling under reflux. After a further hour under reflux, the whole is diluted with 75 ml of cyclohexane and, after cooling, the substance that has crystallised out is filtered off with suction. After washing with a mixture of diethyl ether and hexane (1:1), there is obtained 1-(o-chlorobenzyl)-1H-1,2,3-triazole-4,5-dicarboxylic acid dimethyl ester having a melting point of 88°–91°.

EXAMPLE 13

2.7 g (10 mmol) of 1-(o-chlorobenzyl)-5-methoxy-1H-1,2,3-triazole-4-carboxylic acid are heated under reflux for 30 minutes with 15 ml of thionyl chloride. The excess thionyl chloride is distilled off in vacuo at 60° and the remaining 1-(o-chlorobenzyl)-5-methoxy-1H-1,2,3-triazole-4-carboxylic acid chloride is dissolved in 20 ml of toluene. This toluene solution is added dropwise at 0°–5° to 20 ml of a concentrated aqueous ammonia solution. The precipitated product is filtered off with suction and washed several times with water. 1-(o-chlorobenzyl)-5-methoxy-1H-1,2,3-triazole-4-carboxamide having a melting point of 185°–187° is obtained.

The starting material can be prepared, for example, as follows:

A mixture of 8.4 g (50 mmol) of o-chlorobenzyl azide and 8 g (50 mol) of malonic acid diethyl ester in 25 ml of ethanol is added to a solution of 1.15 g (50 mmol) of sodium in 50 ml of ethanol and the whole is left to stand for 20 hours at room temperature.

6.3 g (50 mmol) of dimethyl sulphate are then added dropwise at 10°–20° and after one hour the whole is concentrated by evaporation in vacuo at 25°. The residue is dissolved in ethyl acetate, washed with 1N sodium hydroxide solution and then with water and the whole is again concentrated by evaporation. The remaining oil is crystallised with 50 ml of diethyl ether. In this manner there is obtained 1-(o-chlorobenzyl)-5-methoxy-1H-1,2,3-triazole-4-carboxylic acid ethyl ester having a melting point of 118°–120°.

3.3 g (11.2 mmol) of 1-(o-chlorobenzyl)-5-methoxy-1H-1,2,3-triazole-4-carboxylic acid ethyl ester are dissolved in 50 ml of warm ethanol and, after the addition of 15 ml of 1N sodium hydroxide solution, heated for 1 hour under reflux. The precipitated sodium salt is dissolved by the addition of 250 ml of water and then acidified with 15 ml of 2N hydrochloric acid. The precipitated product is filtered off with suction and washed with water. In this manner there is obtained 1-(o-chlorobenzyl)-5-methoxy-1H-1,2,3-triazole-4-carboxylic acid having a melting point of 130°–135° (with decarboxylation).

EXAMPLE 14

6.4 g (27 mmol) of 1-(o-chlorobenzyl)-1H-1,2,3-triazole-4-carboxylic acid are heated under reflux for 1 hour with 50 ml of thionyl chloride. The excess thionyl chloride is then distilled in vacuo, the remaining 1-(o-chlorobenzyl)-1H-1,2,3-triazole-4-carboxylic acid chloride is dissolved in 50 ml of toluene and this solution is added dropwise at 5°–10° to 50 ml of a concentrated aqueous ammonia solution. The precipitated product is filtered off with suction, washed with water, and recrystallised from dioxan/ethanol. In this manner there is obtained 1-(o-chlorobenzyl)-1H-1,2,3-triazole-4-carboxamide having a melting point of 237°–239°.

In analogous manner, 1-(o-chlorobenzyl)-1H-1,2,3-triazole-5-carboxamide having a melting point of 155°–158° can also be prepared.

The starting materials can be prepared, for example, as follows:

A solution of 16.75 g (100 mmol) of o-chlorobenzyl azide, 7.35 g (100 mmol) of propynecarboxylic acid and 200 ml of toluene is stirred for 24 hours at 50°. After being cooled to room temperature, the precipitated product is filtered off with suction and washed first with toluene and then with diethyl ether. In this manner there is obtained 1-(o-chlorobenzyl)-1H-1,2,3-triazole-4-carboxylic acid having a melting point of 175° (with decomposition). After concentration of the filtrates by evaporation and washing the residue with a little toluene, 1-(o-chlorobenzyl)-1H-1,2,3-triazole-5-carboxylic acid having a melting point of 120° (with decomposition) remains.

EXAMPLE 15

A mixture of 25.2 g (100 mmol) of 1-(o-chlorobenzyl)-5-methyl-1H-1,2,3-triazole-4-carboxylic acid and 100 ml of thionyl chloride is heated under reflux for 30 minutes. The excess thionyl chloride is then removed in vacuo and the remaining 1-(o-chlorobenzyl)-5-methyl-1H-1,2,3-triazole-4-carboxylic acid chloride is dissolved in 100 ml of toluene. This solution is added dropwise at 5°–10° to 100 ml of a concentrated aqueous ammonia solution, the precipitated product is filtered off with suction and washed with water. After crystallisation from ethanol, 1-(o-chlorobenzyl)-5-methyl-1H-1,2,3-triazole-4-carboxamide having a melting point of 181°–183° is obtained.

The starting material can be prepared, for example, as follows:

14.3 g (110 mmol) of ethyl acetoacetate and 16.8 g (100 mmol) of o-chlorobenzyl azide are added to a solution of 2.53 g (110 mmol) of sodium in 100 ml of ethanol, and the whole is then heated under reflux for 20 hours.

After the addition of 100 ml of 1N sodium hydroxide solution the whole is heated under reflux for a further 2 hours and then, while still warm, acidified with hydrochloric acid. The precipitated product is filtered off with suction and washed with water. After crystallisation from ethanol, there is obtained 1-(o-chlorobenzyl)-5-methyl-1H-1,2,3-triazole-4-carboxylic acid having a melting point of 186°–187° (with decarboxylation).

EXAMPLE 16

A solution of 14.7 g (100 mmol) of o-methylbenzyl azide and 8.3 g (100 mmol) of but-2-ynecarboxamide in 20 ml of dioxan is heated for 16 hours at 100°. After evaporation of the dioxan, the isomers are separated by column chromatography.

In this manner there is obtained 1-(o-methylbenzyl)-5-methyl-1H-1,2,3-triazole-4-carboxamide having a melting point of 185°–187° (from ethanol), as well as a by-product which is discarded.

EXAMPLE 17

In a manner analogous to that described in Example 1, by reacting o-chlorobenzyl azide with 2-cyano-N,N-dimethylacetamide there is obtained 5-amino-1-(o-chlorobenzyl)-1H-1,2,3-triazole-4-(N,N-dimethyl)-carboxamide having a melting point of 143°–145° (from acetonitrile).

EXAMPLE 18

In a manner analogous to that described in Example 2, by reacting 2,3-dichlorobenzyl azide with cyanoacetamide there is obtained 5-amino-1-(2,3-dichlorobenzyl)-1H-1,2,3-triazole-4-carboxamide having a melting point of 224°–226° (from ethanol). The starting material can be produced from 2,3-dichlorobenzyl alcohol as starting material by halogenation, for example with phosphorus tribromide, and reaction with sodium azide.

EXAMPLE 19

10.4 g of crude, approximately 65% strength 1-(o-chlorobenzyl)-1H-1,2,3-triazole-4,5-dicarboxylic acid dimethyl ester are suspended in 50 ml of a 4N solution of ammonia in methanol and the suspension is stirred for 1 hour at 50°. The whole is allowed to cool and filtered with suction and 1-(o-chlorobenzyl)-1H-1,2,3-triazole-4,5-dicarboxamide, which is moderately soluble in dioxane, is dissolved out of the filter cake using dioxane. It precipitates in the form of crystals having a melting point of 222°–224° when the dioxan solution is concentrated and cooled.

The starting material can be produced, for example, as follows:

1.15 g (50 mmol) of sodium are dissolved in 100 ml of methanol. 9.25 g (50 mmol) of 1,2,3-triazole-4,5-dicarboxylic acid dimethyl ester and 8.05 g (50 mmol) of o-chlorobenzyl chloride are added thereto and the whole is boiled for 24 hours. The reaction mixture is then concentrated until crystallisation begins, allowed to cool and filtered with suction. The residue can then be used, after drying, without purification.

EXAMPLE 20

In a manner analogous to that described in Example 6, starting from 2,4,6-trimethylbenzyl alcohol there is obtained via 2,4,6-trimethylbenzyl azide 5-amino-1-(2,4,6-trimethylbenzyl)-1H-1,2,3-triazole-4-carboxamide having a melting point of 195°–196° (from ethyl acetate).

EXAMPLE 21

In a manner analogous to that described in Example 2, starting from m-trifluoromethylbenzyl chloride, there is obtained via m-trifluoromethylbenzyl azide 5-amino-1-(m-trifluoromethyl)-1H-1,2,3-triazole-4-carboxamide having a melting point of 206°–207° (from ethanol).

EXAMPLE 22

In a manner analogous to that described in Example 14, starting from 11.8 g (50 mmol) of 1-(o-chlorobenzyl)-1H-1,2,3-triazole-4-carboxylic acid, converting this into the acid chloride and treating the latter with piperidine (50 mmol), there is obtained 1-(o-chlorobenzyl)-1H-1,2,3-triazole-4-carboxylic acid piperidide having a melting point of 141°–142° (from ethanol) and, by treating the acid chloride with dimethylamine (50 mmol), there is obtained 1-(o-chlorobenzyl)-1H-1,2,3-triazole-4-carboxylic acid N,N-dimethylamide having a melting point of 120°–121° (from ethanol).

EXAMPLE 23

In a manner analogous to that described in Example 1, starting from m-methylbenzyl azide, there is obtained 5-amino-1-(m-methylbenzyl)-1H-1,2,3-triazole-4-carboxamide having a melting point of 200°–202° (from ethanol).

EXAMPLE 24

In a manner analogous to that described in Example 15, starting from m-chlorobenzyl azide, there is obtained via 1-(m-chlorobenzyl)-1H-1,2,3-triazole-4-carboxylic acid having a melting point of 174°–176° (with decomposition) 1-(m-chlorobenzyl)-1H-1,2,3-triazole-4-carboxamide having a melting point of 223°–224° (from ethanol).

EXAMPLE 25

In a manner analogous to that described in Example 15, starting from m-trifluoromethylbenzyl azide, there is obtained via 1-(m-trifluoromethylbenzyl)-1H-1,2,3-triazole-4-carboxylic acid having a melting point of 171° (with decomposition) 1-(m-trifluoromethylbenzyl)-1H-1,2,3-triazole-4-carboxylic acid amide having a melting point of 193°–195° (from ethanol).

EXAMPLE 26

10,1 g of 5-amino-1-(o-chlorobenzyl)-1H-triazole-4-carboxamide are added, portionwise with stirring, to a mixture of 30,7 g of acetanhydride and 0,1 ml of sulphuric acid and heated to 60°. Stirring is continued for additional 30 minutes at 60° to 70°, the reaction mixture is poored into 250 ml of ethanol, heated to reflux for 30 minutes and evaporated in vacuo to dryness. The residue is triturated with 250 ml of ethyl acetate, the crystalline precipitate is collected and re-crystallised from ethyl acetate yielding 5-acetylamino-1-(o-chlorobenzyl)-1H-1,2,3-triazole-4-carboxamide of m.p. 181°–183°.

The ethylacetate mother liquors are combined and evaporated to dryness. The residue is purified chromatographically by means of silica gel and toluene-/ethyl acetate. The eluate is evaporated to dryness and re-crystallised from toluene yielding 5-acetylamino-1-(o-chlorobenzyl)-1H-1,2,3-triazole-4-(N-acetyl)carboxamide of m.p. 140°–142°.

EXAMPLE 27

In an analogous manner as described in Examples 1 to 26 also the following compounds can be prepared:
1-(o-chlorobenzyl)-5-formylamino-1H-1,2,3-triazole-4-carboxamide,
1-(o-chlorobenzyl)-5-formylamino-1H-1,2,3-triazole-4-(N-formyl)carboxamide and
1-(2,6-dichlorobenzyl)-1H-1,2,3-triazole-4-carboxamide.

EXAMPLE 28

In an analogous manner as described in Example 1, starting from 2,6-difluorobenzyl azide 5-amino-1-(2,6-difluorobenzyl)-1H-1,2,3-triazole 4-carboxamide of m.p. 208°-211° (from ethanol) is obtained.

EXAMPLE 29

In an analogous manner as described in Example 12, by reaction of 59 g 1-(o-fluorobenzyl)-1H-1,2,3-triazole-4-carboxylic acid with 300 ml of thionyl chloride and subsequently with ammonia, 1-(o-fluorobenzyl)-1H-1,2,3-triazole-4-carboxamide of m.p. 220°-222° (from ethanol) is obtained.

EXAMPLE 30

In an analogous manner as described in Example 12, by reaction of 1-(2,6-difluorobenzyl)-1H-1,2,3-triazole-4-carboxylic acid with 100 ml of thionyl chloride and subsequently with ammoniac, 1-(2,6-difluorobenzyl)-1H-1,2,3-triazole-4-carboxamide of m.p. 237°-240° (from ethanol) is obtained.

The starting material, 1-(2,6-difluorobenzyl)-1H-1,2,3-triazole-4-carboxylic acid of m.p. 160-163 (decomp.), can be obtained by reacting 36 g of 2,6-difluorobenzyl acide with 15 g propiolic acid in 400 ml toluene at 70°.

In an analogous manner, also 1-(2,3-difluorobenzyl)-1H-1,2,3-triazole-4-carboxamide, 1-(2,4-difluorobenzyl)-1H-1,2,3-triazole-4-carboxamide, 1-(2,5-difluorobenzyl)-1H-1,2,3-triazole-4-carboxamide and 1-(2-chloro-6-fluorobenzyl)-1H-1,2,3-triazole-4-carboxamide, m.p. 274°-276° (from acetic acid), can be manufactured.

EXAMPLE 31

73,5 g of 1-(o-fluorobenzyl)-1H-1,2,3-triazole-4,5-dicarboxylic acid dimethyl ester, dissolved in 1000 ml of methanol, are reacted in an autoklave at 100° for 24 hours with 250 g of ammonia. The suspension resulting from evaporation of excess ammonia, is further evaporated to half of its original volume. The product is filtered off and re-crystallised from dioxane/toluene. 1-(o-fluorobenzyl)-1H-1,2,3-triazole-4,5-dicarboxamide of m.p. 197°-199° is thus obtained. The starting material can be manufactured as follows:

A solution of 41,5 g of o-fluorobenzyl azide and 40 g of acetylenedicarboxylic acid dimethylester in 500 ml of toluene are stirred for 5 hours at 90°. After evaporation of the soluent and re-crystallisation of the residue from ether/petroleum ether 1-(o-fluorobenzyl)-1H-1,2,3-triazole-4,5-dicarboxylic acid dimethyl ether of m.p. 49°-51° is obtained.

The starting material may also be prepared as follows: A solution of 40 g (0.282 mole) of dimethyl acetylenedicarboxylate in 500 ml of toluene is added dropwise to a solution of 41.5 g (0.255 mole) of o-fluorobenzyl azide in 50 ml of toluene, which solution has been heated to 90° C. After a further 5 hours at 90° C., the toluene is stripped off, the reaction mixture is cooled and the crystalline product is filtered with suction. Re-crystallisation from a 1:1 mixture of diethyl ether/petroleum ether yields dimethyl 1-(o-fluorobenzyl)-1H-1,2,3-triazole-4,5-dicarboxylate with a melting point of 49°-51° C.

In an analogous manner, also 1-(2,3-difluorobenzyl)-1H-1,2,3-triazole-4,5-dicarboxamide, 1-(2,4-difluorobenyl) -1H-1,2,3-triazole-4,5-dicarboxamide, 1-(2,5-difluorobenzyl)-1H-1,2,3-triazole-4,5-dicarboxamide, 1-(2-chloro-6-fluoro-benzyl)-1H-1,2,3-triazole-4,5-dicarboxamide , m.p. 214°-216° (from acetic acid), and 1 -(2,6-difluorobenzyl)-1H-1,2,3-triazole-4,5-dicarboxamide of m.p. 203°-205° (from methanol), can be manufactured.

EXAMPLE 32

Also, in a manner analogous to that described in Example 2, starting from m-chlorobenzyl chloride, there is obtained via m-chlorobenzyl azide 5-amino-1-(m-chlorobenzyl)-1H-1,2,3-triazole-4-carboxamide having a melting point of 196°-198° (from ethanol).

EXAMPLE 33

59 g (0.26 mole) of 1-(o-fluorobenzyl)-1H-1,2,3-triazole-4-"carboxylic acid and 300 ml of thionyl chloride are heated for 1 hour to reflux. Excess thionyl chloride is distilled off in vacuo and the residual 1-(o-fluorobenzyl)-1H-1,2,3-triazole-4-carboxylic acid chloride is dissolved in 500 ml of toluene. The solution is added dropwise at 5°-10° C. to 500 ml of a concentrated aqeous ammonia solution. The precipitated product is filtered with suction, washed with water and recrystallised from ethanol, affording 1-(o-fluorobenzyl) -1H-1,2,3-triazole-4-carboxamide with a melting point of 220°-222° C.

The starting material may be prepared as follows: A solution of 50 g (0.33 mole) of o-fluorobenzyl azide, 23.1 g (0.33 mole) of propinecarboxylic acid and 400 ml of toluene is stirred for 24 hours at 70° C. After the reaction mixture has cooled to room temperature, the precipitated product is filtered with suction and washed first with toluene and then with diethyl ether, affording 1-(o-fluorobenzyl)-1H-1,2,3-triazole-4-carboxylic acid with a melting point of 151° C. (dec.).

EXAMPLE 34

Following the procedure described in Example 32 1-(2,6-difluorobenzyl)-1H-1,2,3-triazole-4,5-dicarboxamide with a melting point of 203°-205° C. (recrystallisation from methanol) is obtained from 2,6-difluorobenzyl azide and dimethyl acetylenedicarboxylate via dimethyl 1-(2,6-difluorobenzyl)-1H-1,2,3-triazole-4,5-dicarboxylate.

EXAMPLE 35

Following the procedure described in Example 33, 1-(2,6-difluorobenzyl)-1H-1,2,3-triazole-4-carboxamide with a melting point of 237°-240° C. (recrystallisation from ethanol) is obtained from 2,6-difluorobenzyl azide via 1-(2,6-difluorobenzyl)-1H-1,2,3-triazole-4-carboxylic acid, with a melting point of 160°-162° C. (recrystallisation from acetonitrile; decomposition).

EXAMPLE 36

The following compounds can also be prepared in accordance with the procedures described in Examples 32-35:

1-(2,3-difluorobenzyl)-1H-1,2,3-triazole-4-carboxamide,
1-(2,4-difluorobenzyl)-1H-1,2,3-triazole-4-carboxamide
and
1-(2,5-difluorobenzyl)-1H-1,2,3-triazole-4-carboxamide.

EXAMPLE 37

Following the procedure described in Example 33, 1-(6 chloro-2-fluorobenzyl)-1H-1,2,3-triazole-4-carboxamide with a melting point of 274°-276° C. (recrystallisation from glacial acetic acid) is obtained from 1-(6-chloro-2-fluorobenzyl)-1H-1,2,3-triazole-4-carboxylic acid.

The starting material may be prepared as follows: A mixture of 98 g (0.678 mole) of 6-chloro-2-fluorotoluene, 91.5 g (0.678 mole) of sulfuryl chloride and 0.2 g of dibenzoyl peroxide is stirred for 3 hours at 100°-110° C. and then distilled, affording 6-chloro-2-fluorobenzyl chloride with a boiling point in the range from 78°-82° C.

123 g of (0.687 mole) of 6-chloro-2-fluorobenzyl chloride are added dropwise at 20°-40° C. to a suspension of 47 g (0.722 mole) of sodium azide in 400 ml of dimethylsulfoxide. The mixture is stirred for 4 hours at room temperature, then diluted with ice-water and extracted with cyclohexane. The solvent is removed by distillation and the residue is distilled, affording 6-chloro-2-fluorobenzyl azide; $bp_{15}=99°-100°$ C.

27.5 g (0.15 mole) of 6-chloro-2-fluorobenzyl azide and 10.5 g (0.15 mole) of propinecarboxylic acid in 300 ml of toluene are heated for 3 hours to 90° C. After cooling, the crystals are filtered with suction and recrystallised from acetonitrile to give 1-(6-chloro-2-fluorobenzyl)-1H-1,2,3-triazole-4-carboxylic acid with a melting point of 182° C. (dec.).

EXAMPLE 38

Following the procedure described in Example 32, 1-(6-chloro-2-fluorobenzyl)-1H-1,2,3-triazole-4,5-dicarboxamide with a melting point of 214°-216° C. (recrystallisation from glacial acetic acid) is obtained from 6-chloro-2-fluorobenzyl azide and dimethyl acetylenedicarboxylate via dimethyl 1-(6-chloro-2-fluorobenzyl)-1H-1,2,3-triazole-4,5-dicarboxylate.

EXAMPLE 39

Following the procedure described in Example 32, 1-(2,5-difluorobenzyl)-1H-1,2,3-triazole-4,5-dicarboxamide with a melting point of 191°-192° C. (recrystallisation from dioxane/toluene) is obtained from 2,5-difluorobenzyl azide ($bp_{15}=82°-84°$ C.) via dimethyl 1-(2,5-difluorobenzyl)-1H-1,2,3-triazole-4,5-dicarboxylate.

EXAMPLE 40

Following the procedure described in Example 32, 1-(2,4-difluorobenzyl)-1H-1,2,3-triazole-4,5-dicarboxamide with a melting point of 183°-185° C. (recrystallisation from dioxane/toluene) is obtained from 2,4-difluorobenzyl azide ($bp_{15}=80°-83°$ C.) via dimethyl 1-(2,4-difluorobenzyl)-1H-1,2,3-triazole-4,5-dicarboxylate with a melting point of 75°-76° C. (recrystallisation from cyclohexane).

EXAMPLE 41

Following the procedure described in Example 32, N,N-dimethyl 1-(2,6-difluorobenzyl)-1H-1,2,3-triazole-4,5-dicarboxamide with a melting point of 130°-133° C. (recrystallisation from (tert-butoxymethane) is obtained by reaction with dimethylamine.

EXAMPLE 42

Following the procedure described in Example 32, 1-(2,3-difluorobenzyl)-1H-1,2,3,-triazole-4,5-dicarboxamide with a melting point of 183°-185° C. (recrystallisation from ethyl acetate/benzene) is obtained from 2,3-difluorobenzyl azide and dimethyl acetylenedicarboxylate via dimethyl 1-(2,3-difluorobenzyl)-1H-1,2,3-triazole-4,5-dicarboxylate.

EXAMPLE 43

Following the procedure described in Example 33, 1-(2,6-difluorobenzyl)-5-methyl-1H-1,2,3-triazole-4-carboxamide with a melting point of 208°-210° C. is obtained from 1-(2,6-difluorobenzyl1H-1,2,3,-triazole-4-carboxylic acid.

The starting material is prepared as follows: 2.53 g (0.11 mole) of sodium are dissolved in 60 ml of alcohol, then a mixture of 16.9 g (0.1 mole) of 2,6-difluorobenzyl azide and 14,3 g (0.11 mole) of ethyl acetoacetat in 60 ml of alcohol is added and the batch is heated for 16 hours to reflux. After addition of 120 ml of normal sodium hydroxide solution, the reaction mixture is refluxed for another 2 hours, then diluted with 200 ml of water and acidified to pH 1 with hydrochloric acid while cooling. The precipitated product is filtered with suction, washed first with water and then with ether and dried, affording 1-(2,6-difluorobenzyl)-5-methyl-1H-1,2,3-triazole-4-carboxylic acid with a melting point of 166°-167° C.

EXAMPLE 44

Following the procedure described in Example 32, 1-[1-(2,6-difluorophenyl)ethyl]-1H-1,2,3-triazole-4-carboxamide with a melting point of 205°-207° C. (recrystallisation from methanol) is obtained from ethyl 1-[1-(2,6-difluorophenyl)ethyl]-1H-1,2,3-triazole-4-carboxylate.

The starting material is prepared as follows: Reduction of 10.2 g (66 millimoles) of 2,6-difluoroacetophenone with 2.5 g (65 millimoles) of lithium aluminium hydride in ether affords 1-(2,6-difluorophenyl)ethanol as a colourless oil.

10 g (63 millimoles) of 1-(2,6-difluorophenyl)ethanol are dissolved in 150 ml of hydrazoic acid (1.2N in toluene). To this solution are added 22.8 g (200 millimoles) of trifluoroacetic acid and the reaction mixture is allowed to stand for 24 hours at room temperature. After dilution with 300 ml of hexane, the reaction solution is washed first with water, then with sodium bicarbonate solution until free of acid and dried over sodium sulfate. The solvent is subsequently removed at 40°-50° C. under reduced pressure. The residue is dissolved in 100 ml of hexane and the solution is filtered through 50 g of silica gel and concentrated by evaporation once more, affording 1-(2,6-difluorophenyl)ethyl azide as a colourless oil.

6.5 g (35 millimoles) of 1-(2,6-difluorophenyl)ethyl azide and 2.45 g (35 millimoles) of propinecarboxylic acid in 50 ml of toluene are heated for 24 hours to 60°-70° C. The cooled reaction mixture is extracted with 100 ml of 1N sodium hydroxide solution and the extract is acidified with hydrochloric acid to give 1-[1-(2,6-difluorophenyl)ethyl-1H-1,2,3-triazole-4-carboxylic acid with a melting point of 135°–138° C. (dec.). 7.1 g (26.6 millimoles) of 1-[1-(2,6-difluorophenyl)ethyl]-1H-1,2,3-triazole-4-carboxylic acid, 150 ml of ethanol and 1 ml of sulfuric acid are heated for 10 hours to reflux. Working up gives ethyl 1-[1-(2,6-difluorophenyl)ethyl]-1H-1,2,3-triazole-4-carboxylate with a melting point of 118°–121° C.

EXAMPLE 45

Following the procedure of Example 32, 1-{2-[2-(2,6-difluorophenyl) propyl]}-1H-1,2,3-triazole-4-carboxamide with a melting point of 203°–205° C. (recrystallisation from methanol) is obtained from ethyl 1-{2-[2-(2,6-difluorophenyl)propyl}-1H-1,2,3-triazole-4-carboxylate.

The starting material is prepared as follows: 120 ml of a 3 molar solution of methylmagnesium chloride in tetrahydrofuran are added slowly dropwise to 28 g (150 millimoles) of ethyl 2,6difluorobenzoate in 200 ml of ether. After 1 hour under reflux and working up with 10% ammonium chloride solution, 2-(2,6-difluorophenyl)propan-2-ol with a boiling point of $bp_{12}=74°–76°$ C. is obtained.

20.6 g (120 millimoles) of 2-(2,6-difluorophenyl)propan-2-ol are dissolved in 300 ml of hydrazoic acid solution (1N, in benzene) and 22.8 g (200 millimoles) of trifluoroacetic acid are added to this solution. After 24 hours at room temperature, the reaction solution is diluted with 500 ml of hexane, washed with water and then with sodium bicarbonate until free of acid and dried over sodium sulfate. The solvent is removed by evaporation and the residue is distilled, affording 2-(2,6-difluorophenyl)-2-azidopropane of $bp_{15}=85°–87°$ C.

10 g (51 millimoles) of 2-(2,6-difluorophenyl)-2-azidopropane are reacted with 3.6 g (51 millimoles) of propinecarboxylic acid in 100 ml of toluene and working up is effected as described in Example 12, affording 1-{2-[2-(2,6-difluorophenyl)propyl]}-1H-1,2,3-triazole-4-carboxylic acid with a melting point of 173° C. (dec.). Esterification of the above acid with 50 ml of ethanol and 0.5 ml of concentrated sulfuric acid gives ethyl 1-{2-[2-(2,6-difluorophenyl)propyl]}-1H-1,2,3-triazole-4-carboxylate as a pale yellow viscous oil which can be used for the reaction with ammonia without further purification.

EXAMPLE 46

Following the procedure described in Example 32, 1-{2-[2-(2,6-difluorophenyl)propyl]}-1H-1,2,3-triazole-4,5-dicarboxamide with a melting point of 177°–178° C. (recrystallisation from ethyl acetate/hexane) is obtained from 2-(2,6-difluorophenyl)-2-azidopropane and dimethyl acetylenedicarboxylate via dimethyl 1-{2-[2-(2,6-difluorophenyl)propyl]}-1H-1,2,3-triazole-4,5-dicarboxylate (m.p. 100°–102° C.).

EXAMPLE 47

16.9 g (0.1 mole) of 2,6-difluorobenzyl azide and 8.3 g (0.1 mole) of but-2-ynecarboxamide are heated in 20 ml of dioxane for 16 hours to 100° C. After removing the dioxane by evaporation, the desired isomer is separated by column chromatography, to give 1-(2,6-difluorobenzyl)-5-methyl-1H-1,2,3-triazole-4-carboxamide with a melting point of 208°–210° C. (recrystallisation from methanol).

EXAMPLE 48

2.81 g (10 millimoles) of 1-(2,6-difluorobenzyl)-1H-1,2,3-triazole-4,5-dicarboxamide, 20 ml of acetic anhydride and 2 drops of sulfuric acid are heated for 3 hours to 80° C. After cooling, the mixture is stirred for 1 hour at 20°–25° C. and the precipitated product is filtered with suction and washed with water. Recrystallisation from methanol gives 1-(2,6-difluorobenzyl)-1H-1,2,3-difluorobenzyl)-1H-1,2,3-triazole-4,5-di-(N-acetyl)carboxamide with a melting point of 136°–138° C.

EXAMPLE 49

Following the procedure described in Example 48, 1-(2,6-dif.uorobenzyl)-1H-1,2,3-triazole-4-(N-acetyl)-carboxamide with a melting point of 205°–207° C. (recrystallisation from dioxane/toluene) is also obtained.

EXAMPLE 50

Tablets which each contain 50 mg of 1-(o-fluorobenzyl)-1H -1,2,3-triazole-4-carboxamide may be prepared as follows:

| Composition (for 10,000 tablets) | |
|---|---|
| active ingredient | 500.0 g |
| lactose | 500.0 g |
| potato starch | 352.0 g |
| gelatin | 8.0 g |
| talcum | 60.0 g |
| magnesium stearate | 10.0 g |
| silica (highly dispersed) | 20.0 g |
| ethanol | q.s. |

The active ingredient is mixed with the lactose and 292 g of potato starch and this mixture is moistened with an alcoholic solution of the gelatin and granulated through a sieve. After drying, the granulate is mixed with the remainder of the potato starch, the talcum, the magnesium stearate and the highly disperse silica and the mixture is compressed to tablets weighing 145.0 g each and containing 50.0 mg of active ingredient. If desired, the tablets may be provided with a breaking notch for a finer adjustment of the dose.

EXAMPLE 51

Film-coated tablets each containing 100 mg of 1-(o-fluorobenzyl)-1H-1,2,3-triazole-4-carboxamide may be prepared as follows:

| Composition (for 1000 tablets) | |
|---|---|
| active ingredient | 100.00 g |
| lactose | 100.00 g |
| corn starch | 70.00 g |
| talcum | 8.50 g |
| calcium stearate | 1.50 g |
| hydroxypropylmethyl cellulose | 2.36 g |
| shellac | 0.64 g |
| water | q.s. |
| methylene chloride | q.s |

The active ingredient, the lactose and 40 g of the corn starch are mixed and moistened with a paste prepared from 15 g of corn starch and water (with heating) and the mixture is granulated. The granulate is dried and mixed with the remainder of the corn starch, talcum and the calcium stearate. The mixture is compressed to tablets weighing 280 g. The tablets are then coated with a solution of the hydroxypropylmethyl cellulose and the shellac in methylene chloride. The tablets have a final weight of 283 g.

EXAMPLE 52

Tablets and coated tablets containing another compound of Examples 32-49 can also be prepared as described in Examples 50 and 51.

EXAMPLE 53

Tablets, each containing 50 mg of 5-amino-1-(o-methylbenzyl)-1H-1,2,3-triazole-4-carboxamide, can be manufactured, for example, as follows:

| Composition (10000 tablets) | |
|---|---|
| active ingredient | 500.0 g |
| lactose | 500.0 g |
| potato starch | 352.0 g |
| gelatine | 8.0 g |
| talc | 60.0 g |
| magnesium stearate | 10.0 g |
| silica (highly dispersed) | 20.0 g |
| ethanol | q.s. |

The active ingredient is mixed with the lactose and 292 g of potato starch, and the mixture is moistened with an alcoholic solution of the gelatine and granulated through a sieve. After drying, the whole is mixed with the rest of the potato starch, the talc, the magnesium stearate and the highly dispersed silica, and the mixture is compressed to form tablets each weighing 145.0 mg and containing 50.0 mg of active ingredient; these tablets can, if desired, be provided with break notches for more accurate control of the dose.

EXAMPLE 54

Lacquered tablets, each containing 100 mg of 5-amino-1-(o-methylbenzyl)-1H-1,2,3-triazole-4-carboxamide, can be manufactured as follows:

| Composition (for 1000 tablets) | |
|---|---|
| Active ingredient | 100.00 g |
| lactose | 100.00 g |
| corn starch | 70.00 g |
| talc | 8.50 g |
| calcium stearate | 1.50 g |
| hydroxypropylmethylcellulose | 2.36 g |
| shellac | 0.64 g |
| water | q.s. |
| methylene chloride | q.s. |

The active ingredient, the lactose and 40 g of the corn starch are mixed, moistened with a paste manufactured from 15 g of corn starch and water (while heating), and granulated. The granules are dried, and the remainder of the corn starch, the talc and the calcium stearate are added and mixed with the granules. The mixture is compressed to form tablets (weight: 280 mg) and the tablets are lacquered with a solution of the hydroxypropylmethylcellulose and shellac in methylene chloride: final weight of the lacquered tablet: 283 mg.

EXAMPLE 55

In a manner analogous to that described in Examples 54 and 55 it is also possible to manufacture tablets or lacquered tablets containing a different compound according to any one of Examples 1-31.

We claim:

1. A 1-phenyl-lower alkyl-1H-1,2,3-triazole compound of the formula

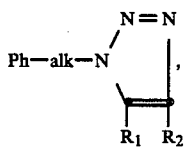

in which
Ph represents phenyl substituted by up to and including 3 substituents selected from lower alkyl, halogen and trifluoromethyl, alk represents lower alkylidene, and wherein either
$R_1$ represents hydrogen, lower alkyl, lower alkoxy amino, N-lower alkylamino, N,N-di-lower alkylamino, N-lower alkanoylamino, carbamoyl, N-lower alkanoylcarbamoyl, N-lower alkylcarbamoyl or N,N-di-lower alkylcarbamoyl and
$R_2$ represents carbamoyl, N-lower alkanoylcarbamoyl, N-lower alkylcarbamoyl or N,N-di-lower alkylcarbamoyl, or
$R_1$ represents carbamoyl, N-lower alkanoylcarbamoyl, N-lower alkylcarbamoyl or N,N-di-lower alkylcarbamoyl and
$R_2$ represents hydrogen or lower alkyl.

2. A compound claimed in claim 1, in which
Ph represents phenyl substituted by up to and including 3 substituents selected from lower alkyl, halogen and trifluoromethyl, alk represents lower alkylidene, and wherein either
$R_1$ represents hydrogen, lower alkyl, lower alkoxy amino, N-lower alkylamino, N,N-di-lower alkylamino, N-lower alkanoylamino, carbamoyl, N-lower alkanoylcarbamoyl, N-lower alkylcarbamoyl or N,N-di-lower alkylcarbamoyl and
$R_2$ represents carbamoyl, N-lower alkanoylcarbamoyl, N-lower alkylcarbamoyl or N,N-di-lower alkylcarbamoyl, or
$R_1$ represents carbamoyl, N-lower alkanoylcarbamoyl, N-lower alkylcarbamoyl or N,N-di-lower alkylcarbamoyl and
$R_2$ represents hydrogen or lower alkyl provided that Ph is different from 2,4-dichlorophenyl and p-methylphenyl, if alk denotes methylene,
$R_1$ denotes amino and $R_2$ denotes carbamoyl.

3. A compound claimed in claim 1, of the formula I in which Ph represents phenyl substituted in the 2-position by lower alkyl, halogen or trifluoromethyl and optionally substituted, in addition, by lower alkyl or halogen, alk represents lower alkylidene, $R_1$ represents hydrogen, lower alkyl, lower alkoxy, amino, N-lower alkylamino, N,N-di-lower alkylamino, carbamoyl, N-lower alkylcarbamoyl or N,N-di-lower alkylcarbamoyl and $R_2$ represents carbamoyl, N-lower alkylcarbamoyl or N,N-di-lower alkylcarbamoyl.

4. A compound claimed in claim 1, of the formula I in which Ph represents 2-halophenyl, 2-trifluoromethylphenyl, 2-lower alkylphenyl, 2,3- or 2,6-dihalophenyl, 2-halo-3-lower alkylphenyl or 3-halo-2-lower alkylphenyl, 2-halo-6-lower alkylphenyl, 2,3- or 2,6-di-lower alkylphenyl, 3-halo-2-trifluoromethylphenyl or 2-halo-3-trifluoromethylphenyl, or 2-halo-6-trifluoromethylphenyl, alk represents 1,1-lower alkylidene, $R_1$ represents hydrogen, lower alkyl, carbamoyl, N-lower alkylcarbamoyl or N,N-di-lower alkylcarbamoyl, and $R_2$ represents carbamoyl, N-lower alkylcarbamoyl or N,N-di-lower alkylcarbamoyl, lower alkyl, lower alkyl in N-lower alkylcarbamoyl and N,N-di-lower alkylcarbamoyl, lower alkoxy and lower alkylidene having up to and including 7 carbon atoms.

5. A compound claimed in claim 1, of the formula I in which Ph represents 2-halophenyl, 2-trifluoromethylphenyl, 2-lower alkylphenyl, 2,3- or 2,6-dihalophenyl, 2-halo-3-lower alkylphenyl or 3-halo-2-lower alkylphenyl, 2-halo-6-lower alkylphenyl, 2,3- or 2,6-di-lower alkylphenyl, 3-halo-2-trifluoromethylphenyl or 2-halo-3-trifluoromethylphenyl, or 2-halo-6-trifluoromethylphenyl, alk represents 1,1-lower alkylidene, $R_1$ represents amino, and $R_2$ represents carbamoyl, N-lower alkylcarbamoyl or N,N-di-lower alkylcarbamoyl, lower alkyl, lower alkyl in N-lower alkylamino or -carbamoyl and N,N-di-lower alkyl-amino or -carbamoyl, lower alkoxy and lower alkylidene having up to and including 7 carbon atoms.

6. A compound claimed in claim 1 of the formula I in which Ph represents phenyl substituted by up to and including 3 substituent selected from lower alkyl groups or halogen atoms and trifluoromethyl, lower alkyl having up to and including 4 carbon atoms and halogen having an atomic number of up to and including 35, alk represents 1,1-lower alkylidene having up to and ingluding 4 carbon atoms, $R_1$ represents amino or lower alkanoylamino of up to and including 7 carbon atoms and $R_2$ represents carbamoyl, N-lower alkanoylcarbamoyl of up to and including 7 carbon atoms, N-lower alkyl-, or N,N-di-lower alkylcarbamoyl having up to and including 4 carbon atoms in each lower alkyl moiety.

7. A compound claimed in claim 1, of the formula I in which Ph represents 2-halophenyl, 2-lower alkylphenyl, 2,3- or 2,6-dihalophenyl, 2,3- or 2,6-di-lower alkylphenyl, a halogen substituent being halogen having an atomic number of up to and including 35 and a lower alkyl substituent having up to and including 4 carbon atoms, or represents 2-trifluoromethylphenyl, alk represents 1,1-lower alkylidene having up to and including 4 carbon atoms, $R_1$ represents amino and $R_2$ represents carbamoyl.

8. A compound claimed in claim 1, of the formula I in which Ph represents 2-halophenyl, 3-halophenyl, 2,6-dihalophenyl, 2-alkylphenyl or 3-trifluoromethylphenyl, alk represents 1,1-lower alkylidene having up to and including 4 carbon atoms, $R_1$ represents amino and $R_2$ represents carbamoyl.

9. A compound claimed in claim 1, of the formula I in which Ph represents 2-halophenyl, 3-halophenyl, 2,6-dihaloplenyl, 2-alkylphenyl or 3-trifluoromethylphenyl, alk represents 1,1-lower alkylidene having up to and including 4 carbon atoms, $R_1$ represents carbamoyl and $R_2$ represents carbamoyl.

10. A compound claimed in claim 1, of the formula I in which Ph represents o-halophenyl or 2,6-dihalophenyl, $R_1$ represents hydrogen or lower alkyl of up to and including 4 carbon atoms and $R_2$ represents carbamoyl.

11. A compound claimed in claim 1 being 5-amino-1-(o-methylbenzyl)-1H-1,2,3-triazole-4-carboxamide.

12. A compound claimed in claim 1 being 1-(2,6-difluorobenzyl)-1H-1,2,3-triazole-4,5-dicarboxamide.

13. A compound claimed in claim 1 being 1-(o-fluoro)-1H-1,2,3-triazole-4,5-dicarboxamide.

14. A compound claimed in claim 1 being 1-(2,6-difluorobenzyl)-1H-1,2,3-triazole-4-carboxamide.

15. A compound claimed in claim 1 being 1-(o-fluorobenzyl)-1H-1,2,3-triazole-4-carboxamide.

16. A compound claimed in claim 1 being 1-(2,6-difluorobenzyl)-1H-1,2,3-triazole-4,5-di-(N-acetyl)carboxamide.

17. A compound claimed in claim 1 being 1-(2-chloro-6-fluoro-benzyl)-1H-1,2,3-triazole-4,5-dicarboxamide.

18. A compound claimed in claim 1 being 1-(2-chloro-6-fluoro-benzyl)-1H-1,2,3-triazole-4-carboxamide.

19. A compound claimed in claim 1 being 1-(2,5-difluorobenzyl)-1H-1,2,3-triazole-4,5-dicarboxamide.

20. An anticonvulsive pharmaceutical composition comprising an anticonvulsively effective amount of a compound claimed in claim 1 in addition to an inert pharmaceutical carrier.

21. A method of treating a convulsive disorder in a warm blooded animal comprising administering to said animal an anticonvulsive effective amount of a compound of formula I

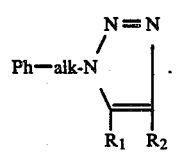

wherein Ph represents phenyl substituted by up to and including three substituents selected from lower alkyl halogen and trifluoromethyl, alk represents lower alkylidene, and wherein either $R_1$ represents hydrogen, lower alkyl, lower alkoxy, amino, N-lower alkyl or N,N-di-lower alkylamino, N-lower alkanoylamino, carbamoyl, N-lower alkanoylcarbamoyl, N-lower alkylcarbamoyl or N,N-di-lower alkylcarbamoyl and $R_2$ denotes carbamoyl, N-lower alkanoylcarbamoyl, N-lower alkylcarbamoyl or N,N-di-lower alkylcarbamoyl or $R_1$ represents carbamoyl, N-lower alkanoylcarbamoyl, N-lower alkylcarbamoyl or N,N-di-lower alkylcarbamoyl and $R_2$ denotes hydrogen or lower alkyl, and wherein lower alkyl lower alkyl in N-lower-amino or -carbamoyl and N,N-di-lower alkylamino or -carbamoyl, lower alkoxy and lower alkylidene have up to and including 7 carbon atoms.

* * * * *